(12) United States Patent
Shitara et al.

(10) Patent No.: US 7,662,841 B2
(45) Date of Patent: Feb. 16, 2010

(54) IMIDAZOTHIAZOLE DERIVATIVES AND PROCESS FOR PRODUCING THE SAME

(75) Inventors: Eiki Shitara, Yokohama (JP); Kunio Atsumi, Tokyo-To (JP); Keiichi Ajito, Kawasaki (JP); Shinya Ikeda, Odawara (JP); Tadashi Katoh, Sendai (JP); Munenori Inoue, Ebina (JP); Mari Nakatani, Sagamihara (JP)

(73) Assignees: Meiji Seika Kaisha, Ltd., Tokyo-To (JP); Sagami Chemical Research Center, Kanagawa-Ken (JP)

( * ) Notice: Subject to any disclaimer, the term of this patent is extended or adjusted under 35 U.S.C. 154(b) by 85 days.

(21) Appl. No.: 11/795,522

(22) PCT Filed: Jan. 19, 2006

(86) PCT No.: PCT/JP2006/300729
§ 371 (c)(1),
(2), (4) Date: Jul. 18, 2007

(87) PCT Pub. No.: WO2006/077919
PCT Pub. Date: Jul. 27, 2006

(65) Prior Publication Data
US 2008/0114164 A1    May 15, 2008

(30) Foreign Application Priority Data
Jan. 19, 2005    (JP)    ............... 2005-011923

(51) Int. Cl.
*A61K 31/429*    (2006.01)
*C07D 235/02*    (2006.01)
(52) U.S. Cl. .................. 514/368; 548/303.1
(58) Field of Classification Search ............. 548/303.1
See application file for complete search history.

(56) References Cited

U.S. PATENT DOCUMENTS 5,371,080 A    12/1994    Hansen et al.

6,825,187 B2 *    11/2004    Kano et al. ............ 514/210.09

FOREIGN PATENT DOCUMENTS

| EP | 0 669 336 | 8/1995 |
|---|---|---|
| JP | 8-311071 | 11/1996 |
| JP | 2005-200412 | 7/2005 |
| WO | 95/14020 | 5/1995 |
| WO | 01/53305 | 7/2001 |
| WO | 2004/055027 | 7/2004 |

OTHER PUBLICATIONS

W. S. Huang et al., "Facile Synthesis of 1-Substituted 5-Trifluoromethylimidazole-4-Carboxylates", Journal of Fluorine Chemistry, vol. 74, pp. 279-282, 1995.
R. I. Fryer et al., "The Synthesis of 4-*H*-Imidazol[5,1-c][1,4]benzothiazine Derivatives", Journal of Heterocyclic Chemistry, vol. 20, No. 6, pp. 1605-1608, Nov.-Dec. 1983.

* cited by examiner

*Primary Examiner*—Rebecca L Anderson
*Assistant Examiner*—Shawquia Young
(74) *Attorney, Agent, or Firm*—Wenderoth, Lind & Ponack, L.L.P.

(57) ABSTRACT

The present invention relates to compounds of formula (I) and a process for producing the same. In formula (I), X represents a halogen atom, and $R^1$ represents group —$COR^2$ wherein $R^2$ represents group OM or C1-12 alkyloxy wherein M represents a hydrogen atom, an alkali metal, an alkaline earth metal, or quaternary ammonium. The use of this compound as a synthetic intermediate can realize the production of carbapenem derivatives having potent antimicrobial activity in an efficient and safe manner at low cost.

(I)

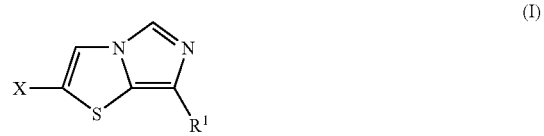

14 Claims, No Drawings

IMIDAZOTHIAZOLE DERIVATIVES AND PROCESS FOR PRODUCING THE SAME

This application is a U.S. national stage of International Application No. PCT/JP2006/300729 filed Jan. 19, 2006.

CROSS-REFERENCE TO RELATED APPLICATIONS

This application is based on Japanese Patent Application No. 011923/2005 (filing date: Jan. 19, 2005), which is a previous Japanese patent application, and claims to enjoy a profit of the right of priority, and the whole disclosure of the previous Japanese application is incorporated herein by reference.

BACKGROUND OF THE INVENTION

1. Field of the Invention

The present invention relates to imidazothiazole derivatives useful as an intermediate for the production of carbapenem derivatives having potent antimicrobial activity and a broad antimicrobial spectrum, and a process for producing the same.

2. Background Art

Carbapenem derivatives have potent antimicrobial activity and a broad antimicrobial spectrum and thus have been energetically studied as a highly useful β-lactam agent.

WO 02/42312 reports finding that carbapenem derivatives having a 7-(1-carbamoylmethylpyridinium-3-yl)carbonylimidazo[5,1-b]thiazole group at the 2-position on the carbapenem ring, that is, compounds of formula (A), have high antimicrobial activity against Gram-positive bacteria and Gram-negative bacteria including MRSA (methicillin resistant *Staphylococcus aureus*), PRSP (penicillin resistant *Streptococcus pneumoniae*), *Haemophilus influenzae*, and β-lactamase producing bacteria, and, at the same time, have high stability against DHP-1(kidney dehydropeptidase-1). Japanese Patent No. 3527003 reports that imidazothiazoles which have been unsubstituted or substituted at the 3-position of the cephem ring, are useful for the development of potent antimicrobial activity. This Japanese Patent No. 3527003 describes substituents in substituted imidazothiazoles which embrace compounds according to the present invention. In the technique disclosed in this patent, however, there is still room for improvement, for example, in procedure process.

Further, WO 2004/055027 reports 2-bromoimidazo[5,1-b]thiazole (a compound of formula (VI')) that is an intermediate important for the substituent at the 2-position on the carbapenem ring in the compound of formula (A). Compounds of formula (A) can be produced according to scheme A from 2-bromoimidazo[5,1-b]thiazole which may be produced according to the present invention.

Scheme A

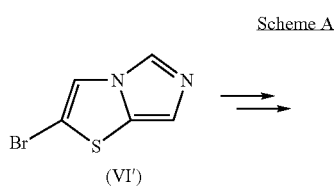

(VI')

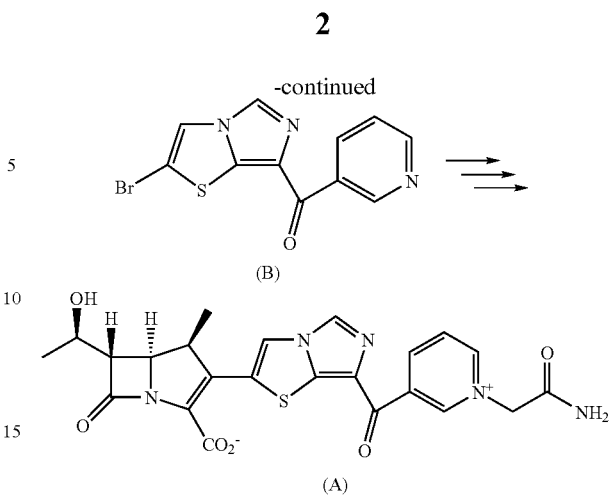

Further, WO 2004/055027 discloses the following scheme B as a process for producing 2-bromoimidazo[5,1-b]thiazole (a compound of formula (VI')).

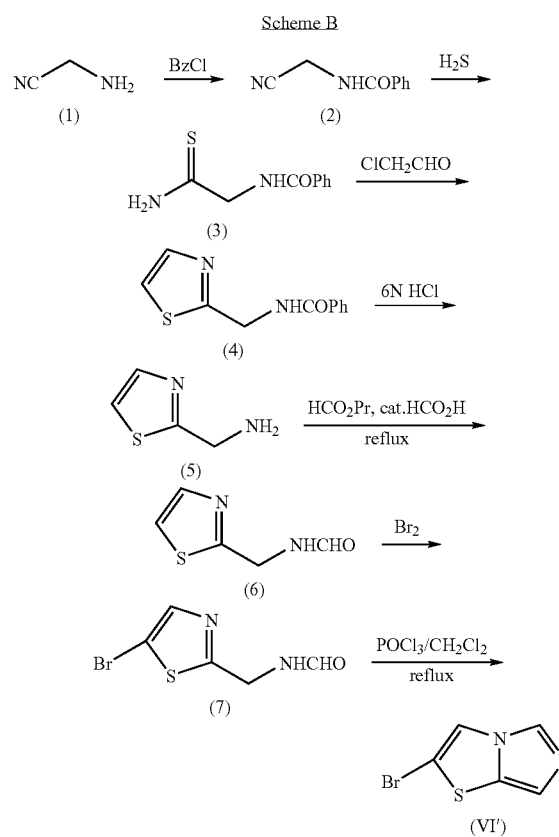

In this scheme B, 2-bromoimidazo[5,1-b]thiazole of formula (VI') as an intermediate important for carbapenem derivatives of formula (A) is produced by reacting a compound of formula (6) produced through five steps using aminoacetonitrile (a compound of formula (1)) as a starting compound with a brominating agent to give a compound of formula (7) and then reacting the compound of formula (7) with a dehydrating agent.

This scheme B, however, involves a cost problem that the compound of formula (1) as the starting compound is expensive and, at the same time, has operational problems that the total number of steps in the scheme is large and, in addition, the step of converting the compound of formula (6) to the compound of formula (7) suffers from a low yield and produces a large amount of decomposition products.

Accordingly, a method for synthesizing 2-bromoimidazo[5,1-b]thiazole, which can use a more inexpensive starting compound, requires a smaller number of steps, and has advantages of production cost and operational improvement, has still been desired.

On the other hand, Journal of Fluorine Chemistry, 1995, 279 reports that isocyanoethyl acetate is reacted with trifluoroacetimidoyl chloride having a substituent on the nitrogen atom in the presence of a base to construct an imidazole ring. This reaction, however, is a monocyclic ring formation reaction for a substituted imidazole, and, so far as the present inventors know, whether or not a bicyclic imidazo[5,1-b]thiazole ring having a different ring construction and a 2-halogenated imidazo[5,1-b]thiazole ring can be constructed in the same manner as described in this document has not been known.

Further, Journal of Heterocyclic Chemistry, 1983, 1605 reports a reaction for decarboxylation by heating an aromatic carboxylic acid in trichlorobenzene under reflux. So far as the present inventors know, however, whether or not this method can be similarly applied to carboxyl group-containing imidazo[5,1-b]thiazole ring derivatives has not been known.

SUMMARY OF THE INVENTION

The present inventors have now succeeded in preparing compounds of formula (I), which will be described later, as an intermediate for the synthesis of carbapenem derivatives of formula (A). The present inventors have succeeded in synthesizing imidazothiazole derivatives of formula (I) which will be described later at high yield by reacting a 2,5-dihalogenated thiazole, derived from 2-aminothiazole which is inexpensively available, with an isocyanoacetic ester. Further, this production process has an operational advantage, can avoid the bromination step, and can synthesize a contemplated compound with higher safety. The present invention has been made based on such finding.

Accordingly, an object of the present invention is to provide a synthetic intermediate that can realize the production of carbapenem derivatives of formula (A) in an efficient and safe manner at a low production cost. That is, an object of the present invention is to provide a novel method for constructing a bicyclic imidazo[5,1-b]thiazole ring.

According to the present invention, there is provided a compound of formula (I):

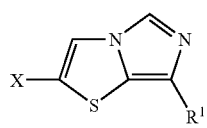

wherein
X represents a halogen atom; and
R$^1$ represents group —COR$^2$;
wherein R$^2$ represents group OM or C1-12 alkyloxy
wherein M represents a hydrogen atom, an alkali metal, an alkaline earth metal, or quaternary ammonium.

There is provided a process for producing a compound of formula (I) according to the present invention, said process comprising the following steps (a) and (b):
(a) reacting a compound of formula (II) with a compound of formula (III) in the presence of a base:

wherein X and X$^1$ each independently represent a halogen atom,

wherein R$^3$ represents C1-12 alkyl, and
(b) optionally further subjecting the compound prepared in step (a) to a hydrolysis reaction.

According to another aspect of the present invention, there is provided a process for producing a compound of formula (VI),

wherein X represents a halogen atom, said process comprising heating a compound of formula (V), a compound of formula (IV), or a compound of formula (V) prepared by hydrolyzing the compound of formula (IV):

wherein X represents a halogen atom; M represents a hydrogen atom, an alkali metal, an alkaline earth metal, or quaternary ammonium, and

wherein X represents a halogen atom; and R$^3$ represents C1-12 alkyl.

According to a further aspect of the present invention, there is provided use of a compound of formula (I) according to the present invention, as a synthetic intermediate for the manufacture of antimicrobial agents.

The use of the compound of formula (I) according to the present invention and the production process thereof can realize the production of compounds of formula (VI), which are an intermediate important for compounds of formula (A), using a more inexpensively available starting material in a smaller number of steps as compared with the prior art technique. Further, according to the present invention, since the conventional bromination step can be avoided, the problem of low yield of this step, the problem of decomposition products, and the operational problem can be avoided, and, at the same time, the safety can be more improved. Further, according to the present invention, the number of steps necessary from the starting compound to the important intermediate can be reduced to the half or less of the number of steps necessary for the prior art technique, and the step involving a low yield can be avoided. At the same time, the yield of the important intermediate and the whole reaction efficiency can be significantly improved (for example, by a factor of 10 or more). As a result, according to the process of the present invention, for example, a production cost reduction and production control can significantly be improved, and carbapenem derivatives (compounds of formula (A)) having excellent antimicrobial activity and a broad antimicrobial spectrum can be efficiently synthesized.

DETAILED DESCRIPTION OF THE INVENTION

Compounds

The term "alkyl" as used herein as a group or a part of a group means alkyl which is of a straight chain, branched chain, or cyclic type or a combination thereof unless otherwise specified. For example, "C1-12" in "C1-12 alkyl" means that the number of carbon atoms in the alkyl group is 1 to 12.

"C1-12 alkyl" is preferably C1-6 alkyl, more preferably C1-4 alkyl, still more preferably C1-3 alkyl. Examples of alkyl include methyl, ethyl, propyl, isopropyl, butyl, isobutyl, s-butyl, t-butyl, pentyl, hexyl, heptyl, octyl, nonyl, decyl, dodecyl, cyclopropyl, cyclobutyl, cyclopentyl, cyclohexyl, cycloheptyl, and cyclooctyl. Preferred are methyl, ethyl, propyl, isopropyl, butyl, isobutyl, s-butyl, t-butyl, cyclopropyl, and cyclobutyl.

Likewise, the term "alkyloxy" as used herein as a group or a part of a group means alkyloxy which is of a straight chain, branched chain, or cyclic type or a combination thereof unless otherwise specified. For example, "C1-12" in "C1-12 alkyloxy" means that the number of carbon atoms in the alkyloxy group is 1 to 12.

"C1-12 alkyloxy" is preferably C1-6 alkyloxy, more preferably C1-4 alkyloxy, still more preferably C1-3 alkyloxy. Examples of alkyloxy include methyloxy, ethyloxy, propyloxy, isopropyloxy, butyloxy, isobutyloxy, s-butyloxy, t-butyloxy, pentyloxy, and hexyloxy. More preferred are methyloxy, ethyloxy, propyloxy, isopropyloxy, butyloxy, isobutyloxy, s-butyloxy, and t-butyloxy.

In the present specification, the alkyl and alkyloxy groups may be optionally substituted. Here, for example, "optionally substituted" alkyl means that one or more hydrogen atoms on the alkyl group may be substituted by one or more substituents (which may be the same or different). It will be apparent to a person having ordinary skill in the art that the maximum number of substituents may be determined depending upon the number of substitutable hydrogen atoms on alkyl. This is true of alkyloxy.

Groups by which the alkyl and alkyloxy groups can be substituted include, for example, halogen atoms and alkyloxy, amino, and hydroxyl groups.

The term "halogen atom" as used herein means a fluorine, chlorine, bromine, or iodine atom, preferably a chlorine, bromine, or iodine atom, more preferably a bromine atom.

In the present invention, $R^1$ is as defined above. In one embodiment of the present invention,
X represents a halogen atom; and
$R^1$ represents group —$COR^2$;
  wherein $R^2$ represents group OM or C1-12 alkyloxy wherein M represents a hydrogen atom, an alkali metal, an alkaline earth metal, or quaternary ammonium.

$R^2$ preferably represents group OM or C1-6 alkyloxy, more preferably hydroxyl or C1-3 alkyloxy.

$R^3$ preferably represents C1-6 alkyl, more preferably C1-4 alkyl, still more preferably C1-3 alkyl.

X preferably represents a bromine, chlorine or iodine atom, more preferably a bromine atom.

$X^1$ preferably represents a bromine, chlorine or iodine atom, more preferably a bromine atom.

M preferably represents a hydrogen atom, a sodium atom, or a potassium atom.

$R^1$ preferably represents group —$COR^2$ wherein $R^2$ represents hydroxyl or C1-6 alkyloxy. In this case, X preferably represents a bromine atom.

$R^1$ more preferably represents group —$COR^2$ wherein $R^2$ represents hydroxyl or C1-4 alkyloxy. In this case, X preferably represents a bromine atom.

Compounds of formula (I) are preferably compounds of formula (IV) or (V). For example, when compounds of formula (I) are of compounds of formula (IV) or (V), preferably, $R^3$ represents a methyl or ethyl group, M represents a hydrogen atom, and X represents a bromine atom.

Compounds described in the working examples may be mentioned as more specific examples of compounds of formula (I).

The compounds according to the present invention may form salts thereof. Such salts include those of formula (I) in which $R^2$ represents a carboxylic acid salt. As described above, such salts include alkali metal salts, alkaline earth metal salts, and quaternary ammonium salts. In the course of or after the formation of the compound according to the present invention, such salts could easily be produced by a person having ordinary skill in the art.

Production Process of Compounds

The production process of compounds of formula (I) according to the present invention, more specifically compounds of formulae (IV) and (V), and the process of producing compounds of formula (A) are as shown in scheme C below.

Scheme I

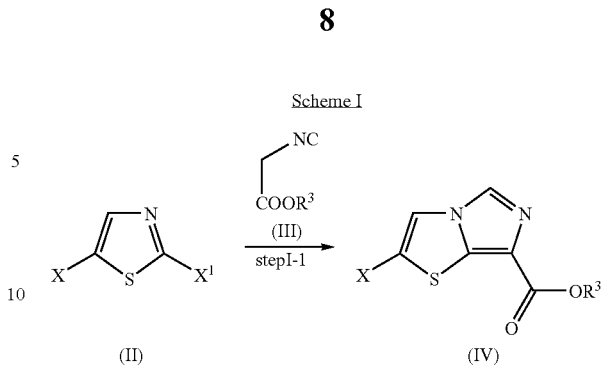

wherein $R^3$, X, and $X^1$ are as defined above.

According to the process shown in scheme I, in step I-1, a compound of formula (IV) is produced by reacting a compound of formula (II) with a compound of formula (III) in the presence of a base. For example, in the above scheme, when $R^3$ represents ethyl and X represents a bromine atom, formula (IV) may be represented by formula (IVa):

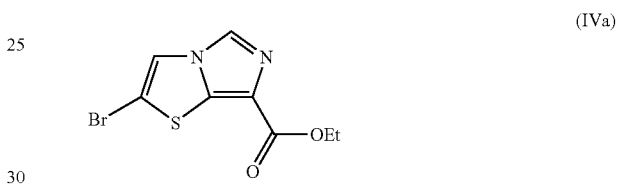

(IVa)

(Step I-1)

In use, the compounds of formulae (II) and (III) in step I-1 may be synthesized, or alternatively may be commercially available. For example, a part of the compounds of formula (II) are available from Aldrich, and a part of the compounds of formula (III) are available, for example, from Tokyo Chemical Industry Co., Ltd.

In this step, an imidazothiazole ring is formed by reacting the compound of formula (II) with the compound of formula (III). A compound of formula (IV) can be produced by reacting the compound of formula (II) with the compound of formula (III) in the presence of a base.

The solvent used in step I-1 is not particularly limited so far as the solvent does not adversely affect the reaction in this step. A person having ordinary skill in the art could properly select the solvent. Example of such solvents include hydrocarbon solvents such as pentane, hexane, benzene, toluene, and xylene, halogenated hydrocarbon solvents such as dichloromethane, 1,2-dichloroethane, chloroform, and carbon tetrachloride, ether solvents such as diethyl ether, tetrahydrofuran, 1,4-dioxane, dimethoxyethane, cyclopentyl methyl ether, aprotic solvents such as acetonitrile, propionitrile, nitromethane, nitroethane, N,N-dimethylformamide, N,N-dimethylacetamide, and dimethyl sulfoxide, and mixed solvents thereof. Ether solvents such as diethyl ether, tetrahydrofuran, and 1,4-dioxane and polar solvents such as N,N-dimethylformamide may be mentioned as preferred solvents.

More preferred solvents include N,N-dimethylformamide and a mixed solvent composed of N,N-dimethylformamide and tetrahydrofuran.

Usable bases include, for example, alkali metal hydrides such as sodium hydride and potassium hydride, alkali metal alkoxides such as potassium-t-butoxide, and sodium-t-butoxide, and alkali metal amides such as lithium diisopropylamide, lithium isopropylcyclohexylamide, lithium dicyclo-

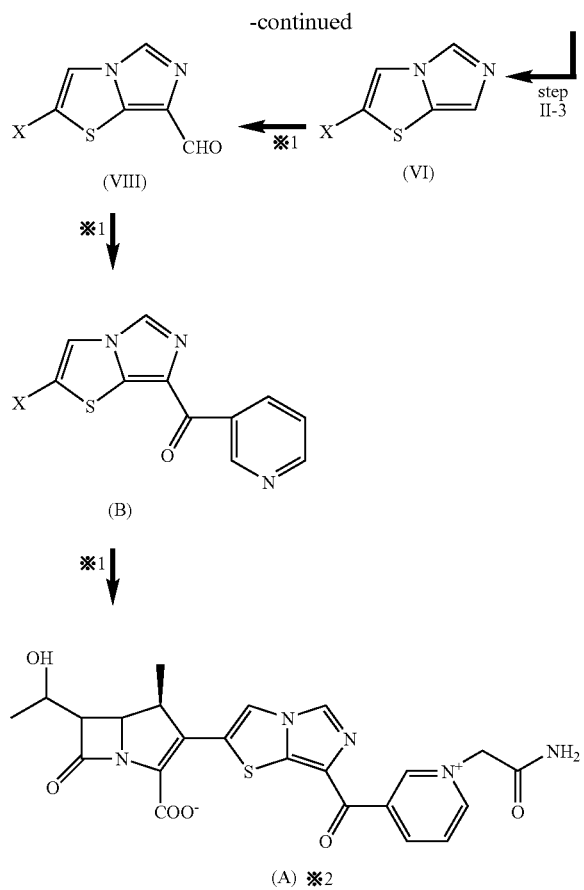

※1 WO2004/055027
※2 WO2002/42312 wherein X, $X^1$, and $R^3$ were as defined above; and $R^4$ represents a chlorine atom or optionally substituted amino.

Production of Compounds of Formula (I)

The process for producing a compound of formula (I) according to the present invention comprises the following steps (a) and (b):

(a) reacting a compound of formula (II) with a compound of formula (III) in the presence of a base; and (b) optionally further subjecting the compound prepared in step (a) to a hydrolysis reaction.

In a preferred embodiment of the present invention, the reaction in step (a) is carried out in a polar solvent in a temperature range of −40° C. to 50° C.

In a more preferred embodiment of the present invention, in the production process of the compound of formula (I), when a hydrolysis reaction is carried out as step (b), a compound of formula (V) is obtained as the compound of formula (I).

The production process of compounds embraced in formula (I) (that is, compounds of formula (IV) or (V)) and compounds of formula (VI) using these compounds will be described in more detail.

Step I: Production of Compounds of Formula (IV)

Compounds of formula (IV) can be synthesized according to scheme I.

hexylamide, lithium bistrimethylsilylamide, sodium bistrimethylsilylamide, and potassium bistrimethylsilylamide. They may also be used in a combination of two or more. Preferred are alkali metal hydrides. Sodium hydride is more preferred.

The reaction temperature range may vary depending, for example, upon the solvent used. In general, however, the reaction temperature range is from −100° C. to the reflux temperature of the solvent used, preferably −40 to 50° C.

The reaction time varies depending, for example, upon the solvent used and the reaction temperature. In general, however, the reaction time is 10 min to 24 hr.

The compound of formula (IV) thus obtained may be subjected to conventional post treatment. The conventional post treatment is treatment that is well known to a person having ordinary skill in the art, and examples thereof include quenching (stopping of the reaction) and extraction. Further, conventional methods such as precipitation, crystallization, gel filtration, and column chromatography on silica gel may be if necessary applied for isolation and purification.

Step II: Production of Compounds of Formulae (V) And (VI)

Compounds of formulae (V) and (VI) may be synthesized according to scheme II.

Preferred are water, methanol, ethanol, and acetonitrile and the like. Water, methanol, and ethanol are more preferred.

Bases include, for example, sodium hydroxide, potassium hydroxide, lithium hydroxide, sodium carbonate, potassium carbonate, lithium carbonate, and cesium carbonate. Preferred bases include sodium hydroxide, potassium hydroxide, lithium hydroxide, and calcium hydroxide.

Acids include sulfuric acid, hydrochloric acid, phosphoric acid, and acetic acid. Preferred acids include sulfuric acid, hydrochloric acid, and acetic acid.

The reaction temperature range may vary depending, for example, upon the solvent used. In general, however, the reaction temperature range is from −100° C. to the reflux temperature of the solvent used, preferably 0 to 70° C.

The reaction time may vary depending, for example, upon the solvent used and the reaction temperature. In general, however, the reaction time is 10 min to 24 hr, preferably 30 min to 24 hr.

The compound of formula (V) thus obtained may be subjected to conventional post treatment. Further, conventional methods such as precipitation, crystallization, gel filtration, and column chromatography on silica gel may be if necessary applied for isolation and purification. After the completion of

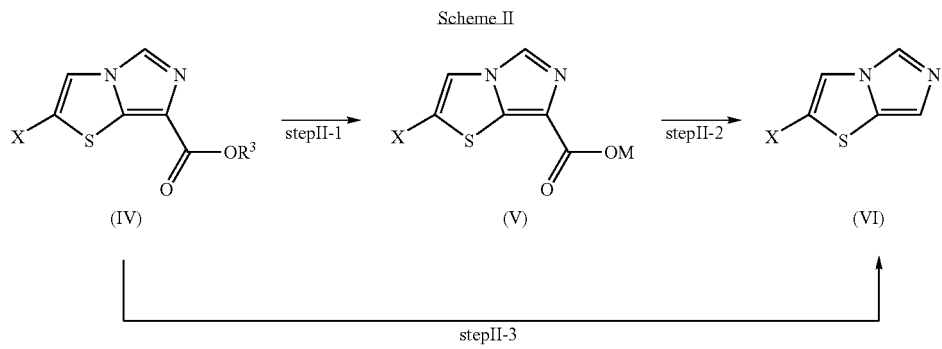

wherein $R^3$, M, and X are as defined above.

A compound of formula (VI) can be produced by hydrolyzing a compound of formula (IV) preferably in the presence of a base to give a compound of formula (V) and heating the compound of formula (V) preferably in a solvent, or directly heating a prepared compound of formula (V) preferably in a solvent. A compound of formula (VI) can also be produced by directly heating the compound of formula (IV) in a solvent.

As described above, the compound of formula (IV) may be produced by reacting a compound of formula (II) with a compound of formula (III) in the presence of a base.

Here, for example, when X represents a bromine atom, formula (VI) may be represented by formula (VI').

(Step II-1 (Step of Hydrolysis))

This step is the step of conducting a hydrolysis reaction of a compound of formula (IV). A compound of formula (V) can be produced by reacting a compound of formula (IV) in the presence of a base or an acid in a solvent that does not adversely affect the reaction.

The solvent used in step II-1 is not particularly limited so far as the solvent does not adversely affect the reaction in this step. The solvent can be properly selected by a person having ordinary skill in the art. Such solvents include, for example, methanol, ethanol, tetrahydrofuran, dioxane, acetonitrile, sulfuric acid, hydrochloric acid, phosphoric acid, acetic acid, and water. Two or more of them may be mixed together to prepare a mixed solvent that may be used as the solvent.

the hydrolysis, the compound of formula (V) may also be isolated as a carboxylic acid salt.

(Step II-2)

This step is the step of conducting a decarboxylation reaction of a compound of formula (V). The compound of formula (VI) can be produced by heating a compound of formula (V) preferably in a solvent.

The solvent used in step II-2 is not particularly limited so far as the solvent does not adversely affect the reaction in this step. The solvent can be properly selected by a person having ordinary skill in the art. Examples of such solvents include dimethyl sulfoxide, 1,3-dimethyl-3,4,5,6-tetrahydro-2(1H) pyrimidinone, 1,2,4-trichlorobenzene, o-dichlorobenzene, xylene, diphenyl ether, ethylene glycol, toluene, acetic acid, acetic anhydride, phosphoric acid, sulfuric acid, and water. Two or more of them may be mixed together to prepare a mixed solvent that be used in this step. The solvent is preferably a single solvent or mixed solvent having a boiling point of 100° C. or above.

More preferred solvents include dimethyl sulfoxide, 1,2,4-trichlorobenzene, o-dichlorobenzene, diphenyl ether, ethylene glycol, toluene, acetic acid, acetic anhydride, sulfuric acid, and water. Still more preferred are 1,2,4-trichlorobenzene, dimethylsulfoxide, diphenyl ether, toluene, ethylene glycol, acetic acid, acetic anhydride, sulfuric acid, water, or a mixed solvent composed of two or more of the above solvents.

Additives may if necessary be added to the solvent. Additives usable herein include, for example, carboxylic acids or anhydrides thereof such as benzoic acid and acetic anhydride, phenols such as phenol and catechol, mineral acids such as hydrochloric acid, sulfuric acid, and hydrobromic acid, metal salts such as lithium chloride, lithium bromide, and lithium iodide, and 1,8-diazabicyclo[5.4.0]-7-undecene. Preferred additives include sulfuric acid, hydrobromic acid, acetic anhydride, benzoic acid, phenol, 1,8-diazabicyclo[5.4.0]-7-undecene. More preferred are sulfuric acid, hydrobromic acid, and acetic anhydride.

The reaction temperature (heating temperature) range may vary depending, for example, upon the solvent used. In general, however, the reaction temperature range is from 80 to 350° C., preferably 100 to 300° C.

The reaction time may vary depending, for example, upon the solvent used and the reaction temperature. In general, however, the reaction time is 10 min to 72 hr, preferably 1 to 48 hr.

The compound of formula (VI) thus obtained may be subjected to conventional post treatment. Further, conventional methods such as precipitation, crystallization, gel filtration, and column chromatography on silica gel may be if necessary applied for isolation and purification.

In another aspect of the present invention, there is provided a process for producing a compound of formula (VI), said process comprising hydrolyzing a compound of formula (IV).

(Step II-3)

This step is the step of conducting a dealkoxycarbonylation reaction of a compound of formula (IV). A compound of formula (VI) can be produced by heating a compound of formula (IV) in a solvent in the presence of an additive.

The solvent used in step II-3 is not particularly limited so far as the solvent does not adversely affect the reaction in this step. The solvent can be properly selected by a person having ordinary skill in the art. Examples of such solvents include dimethyl sulfoxide, 1,3-dimethyl-3,4,5,6-tetrahydro-2(1H)pyrimidinone, 1,2,4-trichlorobenzene, o-dichlorobenzene, xylene, diphenyl ether, ethylene glycol, toluene, sulfuric acid, phosphoric acid, acetic acid, acetic anhydride, propionic acid, and water. Two or more of them may be mixed together to prepare a mixed solvent that be used in this step. Preferably, the solvent has a boiling point of 100° C. or above. More preferred solvents include dimethyl sulfoxide, 1,2,4-trichlorobenzene, sulfuric acid, acetic acid, propionic acid, and water. Still more preferred are dimethyl sulfoxide, propionic acid, sulfuric acid, and water.

Additives usable herein include, for example, sulfonic acids and carboxylic acids such as p-toluenesulfonic acid and benzoic acid, phenol, hydrochloric acid, sulfuric acid, hydrobromic acid, and metal salts such as lithium chloride, lithium bromide, and lithium iodide. Preferred additives include lithium chloride, lithium bromide, lithium iodide, and hydrochloric acid.

The reaction temperature (heating temperature) range may vary depending, for example, upon the solvent used. In general, however, the reaction temperature range is from 80 to 350° C., preferably 100 to 300° C.

The reaction time may vary depending, for example, upon the solvent used and the reaction temperature. In general, however, the reaction time is 10 min to 72 hr, preferably 1 to 24 hr.

The compound of formula (VI) thus obtained may be subjected to conventional post treatment. Further, conventional methods such as precipitation, crystallization, gel filtration, and column chromatography on silica gel may be if necessary applied for isolation and purification.

As shown in the above scheme C, the compound of formula (A), which is the compound of the present invention, may also be produced by step III and step IV through a compound of formula (VIII) using a compound of formula (IV) as a starting compound.

For example, according to step III-1, a compound of formula (VIII) can be produced by subjecting a compound of formula (IV) to a reduction reaction and then oxidizing the reduction product in step III-2.

Alternatively, a compound of formula (VIII) may be produced by either reacting a compound of formula (V) with a commonly used carboxyl group activating agent in step IV-1, or reacting a compound of formula (IV) with an amine compound in step IV-2, to give a compound of formula (IX), and then reducing the compound of formula (IX) in step IV-3. Carboxyl group activating agents include thionyl chloride, oxazalyl chloride, and mixed acid anhydrides.

Production of Compounds of Formula (A)

Carbapenem derivatives of formula (A) having potent antimicrobial activity and a broad antimicrobial spectrum can be produced through a compound of formula (B), for example, according to the method described in WO2004/055027, using the compound of formula (VI) or compound of formula (VIII) synthesized above.

Use of Compounds

Compounds of formula (I) according to the present invention, for example, compounds of formula (IV) or formula (V), are useful as an intermediate for the production of carbapenem derivatives (compounds of formula (A)) containing a 7-(1-carbamoylmethylpyridinium-3-yl)carbonylimidazo[5,1-b] thiazole group at the 2-position on the carbapenem ring.

As disclosed in WO 02/42312, the carbapenem derivatives of formula (A) produced using compounds of formula (I) according to the present invention have high antimicrobial activity against a wide variety of Gram-positive bacteria and Gram-negative bacteria and have high antimicrobial activity against Gram-positive bacteria and Gram-negative bacteria including MRSA, PRSP, Haemophilus influenzae, and β-lactamase producing bacteria. This publication also discloses that these compounds have low toxicity and have high stability against DHP-1. Further, use of these compounds as therapeutic agents for infectious diseases caused by various pathogenic bacteria of animals including humans, and the manufacture of pharmaceutical compositions and chemical products using the above compounds will be apparent to a person having ordinary skill in the art by reference to this publication.

EXAMPLES

The present invention is further illustrated by the following Examples that are not intended as a limitation of the invention.

Synthesis of methyl
2-bromoimidazo[5,1-b]thiazole-7-carboxylate

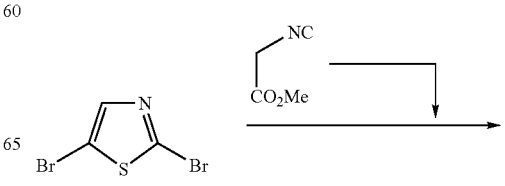

-continued

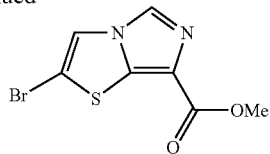

Example 1

Methyl isocyanoacetate (0.63 ml, 6.9 mmol) was gradually added dropwise to a suspension of sodium hydride (60% in mineral oil, 346 mg, 8.6 mmol) in N,N-dimethylformamide (5 ml) in an argon atmosphere under ice cooling, and the mixture was stirred at the same temperature for 2 hr. This solution was added dropwise to a solution of 2,5-dibromothiazole (1.0 g, 4.1 mmol) in tetrahydrofuran (10 ml) cooled to −20° C. (brine/ice water) through a cannula over a period of 15 min, and, while allowing the temperature to rise to about 0° C., the mixture was stirred for 2 hr. After the completion of the reaction, saturated brine was added thereto, and the mixture was extracted with dichloromethane (20 ml×5). The organic layer was dried over anhydrous sodium sulfate, and the solvent was removed by distillation under the reduced pressure. The residue was washed with ethyl acetate to give methyl 2-bromoimidazo[5,1-b]thiazole-7-carboxylate (910 mg, 85%) as a white solid.

$^1$H-NMR (500 MHz, CDCl$_3$): δ 3.95 (3H, s), 7.62 (1H, s), 7.97 (1H, s). $^{13}$C-NMR (125 MHz, CDCl$_3$): δ 51.9, 108.2, 118.6, 121.8, 127.4, 137.8, 162.4. FT-IR (KBr, cm$^{-1}$): 3133, 3033, 3013, 1715, 1507, 1433, 1383, 1343, 1250, 1148, 1046. EI-MS (m/z): 262, 260, 231, 204, 202, 191, 189. Sublimated at 150° C. or above.

Synthesis of ethyl 2-bromoimidazo[5,1-b]thiazole-7-carboxylate

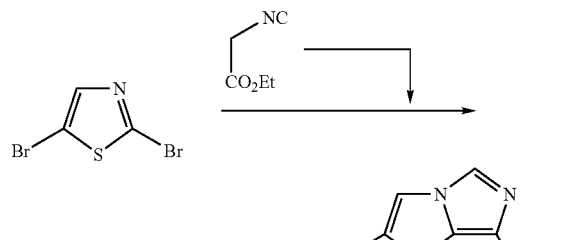

Example 2

Ethyl isocyanoacetate (0.9 ml, 8.2 mmol) was gradually added dropwise to a suspension of sodium hydride (60% in mineral oil, 378 mg, 9.4 mmol) in N,N-dimethylformamide (5 ml) in an argon atmosphere under ice cooling. The mixture was stirred at the same temperature for 2 hr. This solution was added dropwise to a solution of 2,5-dibromothiazole (1.0 g, 4.1 mmol) in tetrahydrofuran (13 ml) cooled to −20° C. (brine/ice water) through a cannula over a period of 20 min, and, while allowing the temperature to rise to around 0° C., the mixture was stirred for 2 hr. After the completion of the reaction, saturated brine was added thereto, and the mixture was extracted with ethyl acetate (20 ml×5). The organic layer was dried over anhydrous sodium sulfate, and the solvent was removed by distillation under the reduced pressure. The residue was washed with ethyl acetate to give ethyl 2-bromoimidazo[5,1-b]thiazole-7-carboxylate. The solvent was removed from the ethyl acetate washing liquor by distillation, and the residue was purified by chromatography on silica gel (hexane:ethyl acetate=1:2). The resultant purification product was combined with the crystal prepared above to give ethyl 2-bromoimidazo[5,1-b]thiazole-7-carboxylate (1.1 g, 90%) as a white solid.

$^1$H-NMR (500 MHz, CDCl$_3$): δ 1.42 (3H, t, J=7.2 Hz), 4.41 (2H, q, J=7.2 Hz), 7.60 (1H, s), 7.96 (1H, s). $^{13}$C-NMR (125 MHz, CDCl$_3$): δ 14.5, 60.9, 108.2, 118.5, 122.1, 127.3, 137.7, 162.0. FT-IR (neat, cm$^{-1}$): 3107, 3008, 1705, 1508, 1475, 1454, 1377, 1338, 1325, 1250, 1159, 1109, 1045, 1022, 953, 837, 771, 644. m.p. 171-172° C. (recrystallized from ethyl acetate)

Example 3

A suspension of sodium hydride (60% in mineral oil, 13.6 g, 368 mmol) in N,N-dimethylformamide (160 ml) was cooled to −10° C. or below under a nitrogen atmosphere. Ethyl isocyanoacetate (36.2 g, 320 mmol) was gradually added dropwise to the cooled suspension, and the mixture was stirred at −3 to 5° C. for 2 hr. This solution was cooled to −20° C. or below and was added dropwise to a solution of 2,5-dibromothiazole (38.8 g, 160 mmol) in N,N-dimethylformamide over a period of about 20 min, and the mixture was stirred at −5 to −20° C. for 2 hr. Water (8 ml) was added thereto to stop the reaction, and the reaction solution was added to 15 wt % brine (960 ml) under ice cooling. Subsequently, the mixture was adjusted to pH 6 to 7 by the addition of 1 M hydrochloric acid. Subsequently, common salt (102 g) was added thereto at the same temperature, and the mixture was stirred overnight. The resultant precipitate was collected by filtration, was washed with water (136 ml), and was dried under the reduced pressure to give ethyl 2-bromoimidazo[5,1-b]thiazole-7-carboxylate (40.4 g, yield 91.9%).

Synthesis of 2-bromoimidazo[5,1-b]thiazole-7-carboxylic acid or its salt

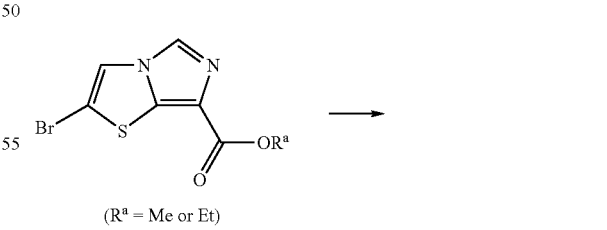

($R^a$ = Me or Et)

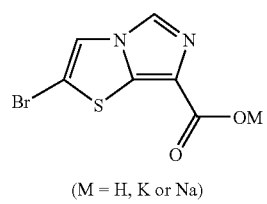

(M = H, K or Na)

Example 4

A 2 M aqueous solution (5 ml) of potassium hydroxide was added to a solution of methyl 2-bromoimidazo[5,1-b]thiazole-7-carboxylate (115 mg, 0.44 mmol) in methanol (20 ml), and the mixture was stirred at room temperature for 19 hr. Methanol was removed by distillation under the reduced pressure to give a potassium salt of 2-bromoimidazo[5,1-b]thiazole-7-carboxylic acid as a white solid. 2 M hydrochloric acid (20 ml) was added thereto under ice cooling to precipitate a solid. The solid was washed with water and was dried under the reduced pressure to give 2-bromoimidazo[5,1-b] thiazole-7-carboxylic acid (97 mg, 89%) as a white solid.

$^1$H-NMR (500 MHz, DMSO-$d_6$): δ 8.28 (1H, s), 8.36 (1H, s), 12.70 (1H, brs). $^{13}$C-NMR (125 MHz, DMSO-$d_6$): δ 105.8, 121.1, 121.3, 129.1, 136.6, 162.7. FT-IR (neat, cm$^{-1}$): 3456, 3140, 1718, 1610, 1514, 1417, 1360, 1338, 1288, 1248, 1216, 1198, 1146, 1117, 1061, 953, 831, 816, 779, 756, 728, 656, 625. Decomposition point 265-270° C.

Example 5

A 2 M aqueous solution (0.35 ml) of sodium hydroxide was added to 2-bromoimidazo[5,1-b] thiazole-7-carboxylic acid (93 mg), and the mixture was stirred at room temperature for one hr. After the completion of the reaction, water was removed by distillation under the reduced pressure. A mixed solvent composed of ethanol and toluene was added to the residue, and the solvent was removed by distillation under the reduced pressure to give a sodium salt of 2-bromoimidazo[5,1-b]thiazole-7-carboxylic acid as a white solid.

Example 6

A 2 M aqueous solution (10 ml) of potassium hydroxide was added to a solution of ethyl 2-bromoimidazo[5,1-b]thiazole-7-carboxylate (265 mg, 0.96 mmol) in methanol (20 ml), and the mixture was stirred at room temperature for 18 hr. Methanol was removed by distillation under the reduced pressure, and the reaction solution was poured into 2 M hydrochloric acid (30 ml) under ice cooling to precipitate a solid. The resultant solid was washed with water, and a mixed solvent composed mainly of ethanol and toluene was added thereto. The solvent was removed by distillation under the reduced pressure, and the residue was thoroughly dried to give 2-bromoimidazo[5,1-b]thiazole-7-carboxylic acid (236 mg, quantitative) as a white solid.

Example 7

A 2 M aqueous solution (35 ml) of potassium hydroxide was added to ethyl 2-bromoimidazo[5,1-b] thiazole-7-carboxylate (1.32 g, 4.80 mmol), and the mixture was stirred at 60° C. for one hr. After the completion of the reaction, the reaction solution was poured into 4 M hydrochloric acid (20 ml) under ice cooling to precipitate a solid. The resultant solid was washed with water, and a mixed solvent composed of ethanol and toluene was added thereto. The solvent was removed by distillation under the reduced pressure, and the residue was then dried to give 2-bromoimidazo[5,1-b]thiazole-7-carboxylic acid (1.08 g, 91%) as a white solid.

Example 8

A suspension of ethyl 2-bromoimidazo[5,1-b] thiazole-7-carboxylate (49.5 g, 200 mmol) in methanol (720 ml) was cooled in a brine/ice water bath. A 2.7 M aqueous solution (720 ml) of sodium hydroxide was added to this suspension, and the mixture was stirred at room temperature for about 15 hr. After the completion of the reaction, methanol was removed by distillation under the reduced pressure for concentration, and the concentrate was cooled in a brine/ice water bath. Concentrated hydrochloric acid (164 ml) was added to this concentrate, and the mixture was adjusted to pH 5 and was stirred at room temperature overnight. The resultant precipitate was collected by filtration. The precipitate was then washed with water (60 ml) and was dried under the reduced pressure to give 2-bromoimidazo[5,1-b]thiazole-7-carboxylic acid (46.5 g, yield 94.0%) as a white solid.

Synthesis of 2-bromoimidazo[5,1-b]thiazole (I)

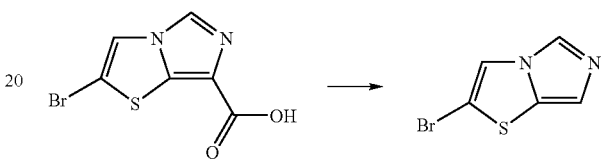

Example 9

A solution of 2-bromoimidazo[5,1-b]thiazole-7-carboxylic acid (27 mg, 0.11 mmol) in 1,2,4-trichlorobenzene (1 ml) was stirred at 210° C. for one hr and then at 220° C. for 30 min. The reaction solution was allowed to cool to room temperature and was diluted with hexane, followed by extraction with 2 M hydrochloric acid (3 ml×3). The aqueous layer was neutralized with a 2 M aqueous solution of sodium hydroxide and was extracted with ethyl acetate (5 ml×3). The organic layer was washed with saturated brine and was dried over anhydrous sodium sulfate. The solvent was removed by distillation under the reduced pressure, and the residue was thoroughly dried to give 2-bromoimidazo[5,1-b]thiazole (18 mg, 80%) as a white solid.

$^1$H-NMR (500 MHz, CDCl$_3$): δ 7.05 (1H, s), 7.48 (1H, s), 7.95 (1H, s). $^{13}$C-NMR (125 MHz, CDCl$_3$): δ 105.7, 117.5, 117.9, 126.6, 129.4. m.p. 77-78° C.

Example 10

A solution of 2-bromoimidazo[5,1-b]thiazole-7-carboxylic acid (1.08 g, 4.37 mmol) in 1,2,4-trichlorobenzene (20 ml) was stirred at 220° C. for 4 hr. The reaction solution was allowed to cool to room temperature, was diluted with hexane, and was extracted with 4 M hydrochloric acid (8 ml×3). The aqueous layer was neutralized with a 10 M aqueous solution of sodium hydroxide and was extracted with ethyl acetate (10 ml×3). The organic layer was washed with saturated brine and was dried over anhydrous sodium sulfate. The solvent was removed by distillation under the reduced pressure, and the residue was purified by column chromatography on silica gel (hexane:ethyl acetate=1:1→1:2) to give 2-bromoimidazo[5,1-b]thiazole (744.8 mg, 84%) as a white solid.

Example 11

Acetic anhydride (0.1 ml, 1.06 mmol) was added to a solution of 2-bromoimidazo[5,1-b]thiazole-7-carboxylic acid (36 mg, 0.14 mmol) in 1,2,4-trichlorobenzene (1 ml), and the mixture was stirred at 130° C. for 24 hr. The reaction solution was allowed to cool to room temperature, was diluted with hexane, and was extracted with 1 M hydrochloric acid (2 ml×3). The aqueous layer was neutralized with a 2 M aqueous solution of sodium hydroxide and was extracted with ethyl acetate (4 ml×3). The organic layer was washed with saturated brine and was dried over anhydrous sodium sulfate. The solvent was removed by distillation under the reduced pressure, and the residue was purified by column chromatography on silica gel (hexane:ethyl acetate =1:1→1:2) to give 2-bromoimidazo[5,1-b]thiazole (22.2 mg, 76%) as a white solid.

Example 12

Acetic anhydride (0.1 ml, 1.06 mmol) was added to a solution of 2-bromoimidazo[5,1-b]thiazole-7-carboxylic acid (38 mg, 0.15 mmol) in 1,2,4-trichlorobenzene (1 ml), and the mixture was stirred at 150° C. for 2 hr. The reaction solution was allowed to cool to room temperature, was diluted with hexane, and was extracted with 1 M hydrochloric acid (2 ml×3). The aqueous layer was neutralized with a 2 M aqueous solution of sodium hydroxide and was then extracted with ethyl acetate (4 ml×3). The organic layer was washed with saturated brine and was dried over anhydrous sodium sulfate. The solvent was then removed by distillation under the reduced pressure, and the residue was purified by column chromatography on silica gel (hexane:ethyl acetate=1:1→1:2) to give 2-bromoimidazo[5,1-b]thiazole (20.5 mg, 66%) as a white solid.

Example 13

A solution of 2-bromoimidazo[5,1-b]thiazole-7-carboxylic acid (22 mg, 0.09 mmol) in dimethyl sulfoxide (1 ml) was stirred at 180° C. for 2 hr. Thereafter, the reaction solution was allowed to cool to room temperature and was then concentrated by removal of the solvent under the reduced pressure. The residue was purified by column chromatography on silica gel (ethyl acetate:methanol=60:1) to give 2-bromoimidazo[5,1-b]thiazole (4 mg, 20%) as a white solid.

Example 14

A solution of 2-bromoimidazo[5,1-b]thiazole-7-carboxylic acid (28 mg, 0.11 mmol) in diphenyl ether (1 ml) was stirred at 220° C. for 1.5 hr. The reaction solution was allowed to cool to room temperature, was diluted with hexane, and was extracted with 2 M hydrochloric acid (3 ml×3). The aqueous layer was neutralized with a 2 M aqueous solution of sodium hydroxide and was extracted with ethyl acetate (5 ml×3). The organic layer was washed with saturated brine and was dried over anhydrous sodium sulfate. The solvent was removed by distillation under the reduced pressure, and the residue was purified by column chromatography on silica gel (ethyl acetate:methanol=60:1) to give 2-bromoimidazo[5,1-b]thiazole (12 mg, 54%) as a white solid.

Example 15

A solution of 2-bromoimidazo[5,1-b]thiazole-7-carboxylic acid (28 mg, 0.11 mmol) in ethylene glycol (1 ml) was stirred at 180° C. for 2.5 hr. The reaction solution was allowed to cool to room temperature, a 2.7 M aqueous solution (5 ml) of sodium hydroxide was added to the cooled solution, and the mixture was extracted with ethyl acetate (5 ml×3). The organic layer was washed with saturated brine and was dried over anhydrous sodium sulfate. The solvent was removed by distillation under the reduced pressure to give 2-bromoimidazo[5,1-b]thiazole (11 mg, 48%) as a crude product.

Example 16

A solution of 2-bromoimidazo[5,1-b]thiazole-7-carboxylic acid (36 mg, 0.14 mmol) in acetic acid (1 ml) was heated under reflux for 2 days. The reaction solution was allowed to cool to room temperature and was then concentrated by removal of the solvent under the reduced pressure, and the residue was purified by column chromatography on silica gel (hexane:ethyl acetate=1:1) to give 2-bromoimidazo[5,1-b]thiazole (4 mg, 14%) as a white solid.

Example 17

A solution of 2-bromoimidazo[5,1-b]thiazole-7-carboxylic acid (31 mg, 0.12 mmol) and phenol (12 mg, 0.12 mmol) dissolved in 1,2,4-trichlorobenzene (1 ml) was stirred at 180° C. for 24 hr. The reaction solution was allowed to cool to room temperature, was diluted with hexane, and was extracted with 1 M hydrochloric acid (3 ml×3). The aqueous layer was neutralized with a 2 M aqueous solution of sodium hydroxide and was extracted with ethyl acetate (5 ml×3). The organic layer was washed with saturated brine and was dried over anhydrous sodium sulfate. The solvent was removed by distillation under the reduced pressure. The residue was purified by column chromatography on silica gel (hexane:ethyl acetate=1:1) to give 2-bromoimidazo[5,1-b]thiazole (13 mg, 50%) as a white solid.

Example 18

A solution of 2-bromoimidazo[5,1-b]thiazole-7-carboxylic acid (32 mg, 0.13 mmol) and benzoic acid (16 mg, 0.13 mmol) dissolved in 1,2,4-trichlorobenzene (1 ml) was stirred at 180° C. for 24 hr. The reaction solution was allowed to cool to room temperature, was diluted with hexane, and was extracted with 2 M hydrochloric acid (3 ml×3). The aqueous layer was neutralized with a 2 M aqueous solution of sodium hydroxide and was extracted with ethyl acetate (5 ml×3). The organic layer was washed with saturated brine and was dried over anhydrous sodium sulfate. The solvent was then removed by distillation under the reduced pressure, and the residue was thoroughly dried to give 2-bromoimidazo[5,1-b]thiazole (13 mg, 49%) as a white solid.

Example 19

A solution of 2-bromoimidazo[5,1-b]thiazole-7-carboxylic acid (34 mg, 0.14 mmol) and 1,8-diazabicyclo[5,4,0]-7-undecene (21 μl, 0.14 mmol) dissolved in 1,2,4-trichlorobenzene (1 ml) was stirred at 180° C. for 5.5 hr. The reaction solution was allowed to cool to room temperature, was diluted with hexane, and was extracted with 2 M hydrochloric acid (3 ml×3). The aqueous layer was neutralized with a 2 M aqueous solution of sodium hydroxide and was extracted with ethyl acetate (5 ml×3). The organic layer was washed with saturated brine and was dried over anhydrous sodium sulfate. The solvent was removed by distillation under the reduced pressure, and the residue was purified by column chromatography on silica gel (hexane:ethyl acetate=1:1) to give 2-bromoimidazo[5,1-b]thiazole (12 mg, 41%) as a white solid.

Example 20

A solution of 2-bromoimidazo[5,1-b]thiazole-7-carboxylic acid (33 mg, 0.13 mmol) in 1,2,4-trichlorobenzene (1 ml) was stirred at 180° C. for 24 hr. The reaction solution was allowed to cool to room temperature, was diluted with hexane, and was extracted with 2 M hydrochloric acid (3 ml×3). The aqueous layer was neutralized with a 2 M aqueous solution of sodium hydroxide and was then extracted with ethyl acetate (5 ml×3). The organic layer was washed with saturated brine and was dried over anhydrous sodium sulfate. The solvent was removed by distillation under the reduced pressure, and the residue was thoroughly dried to give 2-bromoimidazo[5,1-b]thiazole (5 mg, 15%) as a white solid.

Example 21

2-Bromoimidazo[5,1-b]thiazole-7-carboxylic acid (34.8 g, 141 mmol) was suspended in a mixed solvent composed of water (320 ml) and acetic acid (480 ml). Concentrated sulfuric acid (29.5 g, 301 mmol) was added to the suspension at room temperature, and the mixture was stirred at 105° C. for about 24 hr. After the completion of the reaction, sodium carbonate (35.1 g, 331 mmol) was added to the reaction solution, and the mixture was concentrated by removal of the solvent by distillation under the reduced pressure. Water (320 ml) was added to the concentrate, and the solvent was removed by distillation under the reduced pressure. Thereafter, water (200 ml) and ethyl acetate (400 ml) were again added to the residue, and the mixture was adjusted to pH 7 by the addition of a 25 wt % aqueous solution of sodium hydroxide with stirring. The insolubles were removed by filtration, followed by separation. The aqueous layer was extracted with ethyl acetate twice (200 ml, 100 ml). The organic layers were combined and were washed with 15 wt % brine (100 ml). After washing, while concentrating the washed organic layers, the solvent was replaced with hexane to crystallize 2-bromoimidazo[5,1-b]thiazole. The crystallizing liquid was cooled to 5° C. or below and was stirred overnight, and the crystals were collected by filtration. The crystals were washed with hexane (80 ml) and were dried under the reduced pressure to give 2-bromoimidazo[5,1-b]thiazole (26.0 g, yield 90.8%) as a white solid.

Example 22

2-Bromoimidazo[5,1-b]thiazole-7-carboxylic acid (0.52 g, 2.10 mmol) was suspended in a mixed solvent composed of water (4.0 ml) and acetic acid (6.0 ml). 48 wt % hydrobromic acid (0.75 g, 4.42 mmol) was added to the suspension at room temperature, and the mixture was stirred at 105° C. for about 22 hr. After the completion of the reaction, ethyl acetate (5 ml), a 25 wt % aqueous solution of sodium hydroxide (10 ml), and sodium carbonate (1.63 g, 15.38 mmol) were added to the reaction solution. The mixture was adjusted to pH 6, followed by separation. After the separation, the aqueous layer was extracted twice with 5 ml of ethyl acetate. Thereafter, the organic layers were combined, were washed with 15 wt % brine (5 ml), were then dehydrated over magnesium sulfate, and were evaporated to dryness. The residue was further dried under the reduced pressure with an oil pump to give 2-bromoimidazo[5.1-b]thiazole (0.40 g, yield 93.8%) as a white solid.

Example 23

2-Bromoimidazo[5,1-b]thiazole-7-carboxylic acid (0.52 g, 2.10 mmol) was suspended in a mixed solvent composed of water (4.0 ml) and acetic acid (6.0 ml). Concentrated hydrochloric acid (0.30 g, 3.04 mmol) was added to the suspension at room temperature, and the mixture was stirred at 105° C. for about 19 hr. After the completion of the reaction, sodium carbonate (0.44 g, 4.15 mmol) was added to the reaction solution, and the mixture was concentrated by removal of the solvent by distillation under the reduced pressure. Water (10 ml) was added to the concentrate. Further, the solvent was removed by distillation under the reduced pressure, and water (10 ml) and ethyl acetate (5 ml) were again added thereto. The mixture was adjusted to pH 6 by the addition of a 2 M aqueous solution of sodium hydroxide with stirring. After the separation, the aqueous layer was extracted twice with 5 ml of ethyl acetate. Thereafter, the organic layers were combined and were washed with 15 wt % brine (5 ml). While concentrating the washed organic layers, the solvent was replaced with methanol (3 ml), and 10 ml of water was added thereto to crystallize 2-bromoimidazo[5,1-b]thiazole. The crystallizing liquid was cooled to 5° C. or below and was stirred overnight. The crystals were then collected by filtration. The resultant precipitate was dried under the reduced pressure to give 2-bromoimidazo[5.1-b]thiazole (0.39 g, yield 91.4%) as a white solid.

Synthesis of 2-bromoimidazo[5,1-b]thiazole (II)

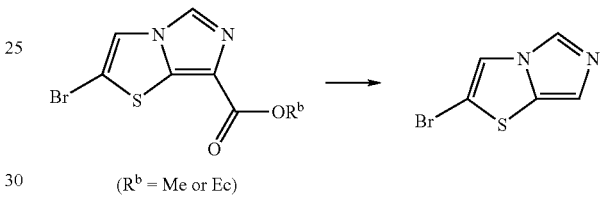

($R^b$ = Me or Ec)

Example 24

Water (2.5 µl, 0.14 mmol) was added to a solution of methyl 2-bromoimidazo[5,1-b]thiazole-7-carboxylate (36 mg, 0.14 mmol) and lithium iodide (73 mg, 0.55 mmol) in dimethyl sulfoxide (8 ml) solution, and the mixture was stirred at 180° C. for 2 hr. Water was added to the reaction solution, and the mixture was extracted with ethyl acetate (5 ml×3). The organic layer was washed with saturated brine and was dried over anhydrous sodium sulfate. The solvent was removed by distillation under the reduced pressure. The residue was purified by column chromatography on silica gel (hexane:ethyl acetate=1:1) to give 2-bromoimidazo[5,1-b]thiazole (4.5 mg, 16%) as a white solid.

Example 25a

Concentrated hydrochloric acid (0.3 ml) was added to a solution of methyl 2-bromoimidazo[5,1-b]thiazole-7-carboxylate (54 mg, 0.21 mmol) in propionic acid (2 ml), and the mixture was heated under reflux for 11 hr. The reaction solution was neutralized with a 2 M aqueous solution of sodium hydroxide and was extracted with ethyl acetate (7 ml×3). The organic layer was washed with saturated brine and was dried over anhydrous sodium sulfate. The solvent was removed by distillation under the reduced pressure. The residue was purified by column chromatography on silica gel (hexane:ethyl acetate=1:2) to give 2-bromoimidazo[5,1-b]thiazole (12 mg, 28%) as a white solid.

Example 25b

Ethyl 2-bromoimidazo[5,1-b]thiazole-7-carboxylate (2.00 g, 7.3 mmol) was suspended in a mixed solvent composed of water (16 ml) and acetic acid (24 ml), concentrated sulfuric acid (7.84 g, 80.0 mmol) was added to the suspension at room temperature, and the mixture was stirred at 105° C. for about 30 hr. After the completion of the reaction, sodium carbonate (9.32 g, 88.0 mmol) was added to the reaction solution, and acetic acid was removed by distillation under the reduced pressure. Further, water (10 ml) was again added to the concentrate, and the solvent was removed by distillation under the reduced pressure. Water (10 ml) and ethyl acetate (20 ml) were added to the residue, and the mixture was adjusted to pH 7 by the addition of a 25 wt % aqueous solution of sodium hydroxide with stirring. The insolubles were removed by filtration, followed by separation. The aqueous layer was then extracted twice with ethyl acetate (20 ml, 20 ml). The organic layer was washed with 15 wt % brine (20 ml). After washing, while concentrating the organic layer, the solvent was replaced with n-hexane to crystallize 2-bromoimidazo[5,1-b]thiazole. Subsequently, the suspension was cooled to 5° C. or below and was stirred overnight. The crystals were collected by filtration, were washed with n-hexane (20 ml) and were dried under the reduced pressure to give 2-bromoimidazo[5,1-b]thiazole (1.02 g, yield 68.5%) as a white solid.

Synthesis of
2-bromo-7-hydroxymethylimidazo[5,1-b] thiazole
and 2-bromoimidazo[5,1-b]thiazole-7-carbaldehyde

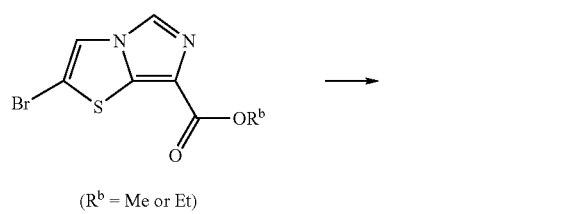

(R$^b$ = Me or Et)

Example 26 (Reference Example)

A solution of methyl 2-bromoimidazo[5,1-b]thiazole-7-carboxylate (31 mg, 0.12 mmol) in dichloromethane (8 ml) was cooled to −100° C. Thereafter, a toluene solution of diisobutylaluminium hydride (1.01 M solution; 0.4 ml, 0.4 mmol) was added dropwise to the cooled solution. The mixture was stirred at −100° C. for 50 min and then at −80° C. for 15 min. After the completion of the reaction, a saturated aqueous potassium sodium tartrate solution was added to the reaction solution, and the mixture was stirred at room temperature for one hr and was extracted with ethyl acetate (8 ml×3). The organic layer was washed with saturated brine and was dried over anhydrous sodium sulfate. The solvent was removed by distillation under the reduced pressure to give 2-bromo-7-hydroxymethylimidazo[5,1-b]thiazole (26 mg, 95%) as a white solid.

$^1$H-NMR (500 MHz, CDCl$_3$): δ 3.09 (1H, brs), 4.75 (2H, s), 7.44 (1H, s), 7.90 (1H, s). $^{13}$C-NMR (125 MHz, CDCl$_3$): δ 58.7, 106.3, 117.9, 125.9, 126.4, 130.0. FT-IR (neat, cm$^{−1}$): 3190, 3130, 1456, 1360, 1070, 1005, 928, 802, 748, 638, 627. m.p. 104-105° C.(recrystallized from chloroform-hexane)

Example 27 (Reference Example)

A solution of ethyl 2-bromoimidazo[5,1-b] thiazole-7-carboxylate (101 mg, 0.37 mmol) in dichloromethane (5 ml) was cooled to −50° C. A toluene solution of diisobutylaluminium hydride (1.01 M solution; 1.1 ml, 1.1 mmol) was then added dropwise to the cooled solution, and the mixture was stirred at the same temperature for 10 min. After the completion of the reaction, a saturated aqueous potassium sodium tartrate solution was added thereto, and the mixture was stirred at room temperature for one hr and was extracted with ethyl acetate (7 ml×3). The organic layer was washed with saturated brine and was dried over anhydrous sodium sulfate, and the solvent was removed by distillation under the reduced pressure to give 2-bromo-7-hydroxymethylimidazo[5,1-b]thiazole (85 mg, 99%) as a white solid.

Example 28 (Reference Example)

A solution of ethyl 2-bromoimidazo[5,1-b] thiazole-7-carboxylate (160 mg, 0.58 mmol) in dichloromethane (6 ml) was cooled to −78° C. A toluene solution of diisobutylaluminium hydride (1.01 M solution; 1.7 ml, 1.75 mmol) was added dropwise to the solution, and the mixture was stirred at the same temperature for 15 min. After the completion of the reaction, a saturated aqueous potassium sodium tartrate solution was added thereto, and the mixture was stirred at room temperature for one hr and was extracted with ethyl acetate (7 ml×3). The organic layer was washed with saturated brine and was then dried over anhydrous sodium sulfate, and the solvent was removed by distillation under the reduced pressure to give 2-bromo-7-hydroxymethylimidazo[5,1-b]thiazole (128 mg, 94%) as a white solid.

Example 29 (Reference Example)

A solution of ethyl 2-bromobonilimidazo[5,1-b] thiazole-7-carboxylate (104 mg, 0.38 mmol) in dichloromethane (5 ml) was cooled to −30° C. A toluene solution of diisobutylaluminium hydride (1.01 M solution; 1.1 ml, 1.1 mmol) was then added dropwise to the cooled solution, and the mixture was stirred at the same temperature for 15 min. After the completion of the reaction, a saturated aqueous potassium sodium tartrate solution was added thereto, and the mixture was stirred at room temperature for 1.5 hr and was extracted with ethyl acetate (7 ml×3). The organic layer was washed with saturated brine and was then dried over anhydrous sodium sulfate. The solvent was removed by distillation under the reduced pressure, and the residue was purified by column chromatography on silica gel (ethyl acetate:methanol=40:1) to give 2-bromo-7-hydroxymethylimidazo[5,1-b]thiazole (76 mg, 86%) as a white solid.

Example 30 (Reference Example)

A solution of ethyl 2-bromoimidazo[5,1-b] thiazole-7-carboxylate (52 mg, 0.19 mmol) in toluene (7 ml) was cooled to −78° C. A toluene solution of diisobutylaluminium hydride (1.01 M solution; 0.65 ml, 0.64 mmol) was added dropwise to the cooled solution, and the mixture was stirred at the same temperature for 40 min. After the completion of the reaction, a saturated aqueous potassium sodium tartrate solution was added thereto, and the mixture was stirred at room temperature for one hr and was extracted with ethyl acetate (5 ml×3). The organic layer was washed with saturated brine and was dried over anhydrous sodium sulfate, and the solvent was removed by distillation under the reduced pressure to give 2-bromo-7-hydroxymethylimidazo[5,1-b]thiazole (44 mg, 99%) as a white solid.

Example 31 (Reference Example)

A solution of ethyl 2-bromoimidazo[5,1-b] thiazole-7-carboxylate (84 mg, 0.31 mmol) in tetrahydrofuran (7 ml) was cooled to −50° C. A toluene solution of diisobutylaluminium hydride (1.01 M solution; 1.06 ml, 1.07 mmol) was added dropwise to the cooled solution, and the mixture was stirred at the same temperature for 15 min. After the completion of the reaction, a saturated aqueous potassium sodium tartrate solution was added thereto, and the mixture was stirred at room temperature for 1.5 hr and was extracted with ethyl acetate (7 ml×3). The organic layer was washed with saturated brine and was then dried over anhydrous sodium sulfate. The solvent was removed by distillation under the reduced pressure, and the residue was purified by column chromatography on silica gel (ethyl acetate:methanol=60:1→30:1) to give 2-bromo-7-hydroxymethylimidazo[5,1-b]thiazole (44 mg, 61%) as a white solid and 2-bromoimidazo[5,1-b]thiazole-7-carbaldehyde (19 mg, 26%) as a white solid.

Synthesis of
2-bromoimidazo[5,1-b]thiazole-7-carbaldehyde (I)

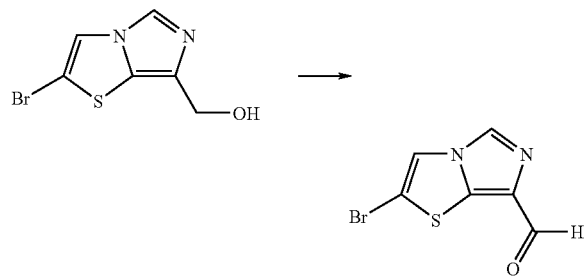

Example 32 (Reference Example)

Manganese dioxide (content 75%; 5.3 g, 46.11 mmol) was added to a solution of 2-bromo-7-hydroxymethylimidazo[5,1-b]thiazole (1.1 g, 4.61 mmol) in dichloromethane (100 ml), and the mixture was heated under reflux for 30 min. After the completion of the reaction, the reaction mixture was filtered through Celite, followed by washing with dichloromethane. The solvent was then removed by distillation under the reduced pressure to give 2-bromoimidazo[5,1-b]thiazole-7-carbaldehyde (989 mg, 93%) as a white solid.

$^1$H-NMR (500 MHz, CDCl$_3$): δ 7.65 (1H, s), 8.01 (1H, s), 9.90 (1H, s). $^{13}$C-NMR (125 MHz, CDCl$_3$): δ 108.9, 118.0, 127.9, 131.4, 136.5, 184.2. FT-IR (neat, cm$^{-1}$): 3136, 3113, 3099, 1637, 1560, 1502, 1446, 1329, 1236, 1198, 1099, 1092, 816, 793, 727, 650, 638. m.p. 200-201° C. (recrystallized from dichloromethane-hexane)

Example 33 (Reference Example)

5% Ru/Al$_2$O$_3$ (101 mg, 0.5 mmol) was added to a solution of 2-bromo-7-hydroxymethylimidazo[5,1-b] thiazole (23 mg, 0.1 mmol) in ethyl acetate (2 ml). The air in the system was replaced with oxygen, and the mixture was stirred at 80° C. for 18 hr. The solvent was removed by distillation under the reduced pressure. The residue was purified by column chromatography on silica gel (ethyl acetate:methanol=60:1) to give 2-bromoimidazo[5,1-b]thiazole-7-carbaldehyde (19 mg, 82%) as a white solid.

Example 34 (Reference Example)

A solution of 2-bromo-7-hydroxymethylimidazo [5,1-b] thiazole (44 mg, 0.19 mmol) in dichloromethane (4 ml) was added to a suspension of pyridinium chlorochromate (121 mg, 0.56 mmol) in dichloromethane (2 ml), and the mixture was stirred at room temperature for 30 min. After the completion of the reaction, the reaction solution was diluted with diethyl ether, anhydrous magnesium sulfate was added thereto, and the mixture was stirred at room temperature for additional 10 min. The reaction mixture was filtered through Celite. The solvent was removed by distillation under the reduced pressure, and the residue was purified by column chromatography on silica gel (ethyl acetate:methanol=60:1) to give 2-bromoimidazo[5,1-b]thiazole-7-carbaldehyde (8 mg, 18%) as a white solid.

Example 35 (Reference Example)

A solution of 2-bromo-7-hydroxymethylimidazo [5,1-b] thiazole (27 mg, 0.11 mmol) in dichloromethane (3.5 ml) was added to a suspension of pyridinium chlorochromate (38 mg, 0.18 mmol) and sodium acetate (4.8 mg, 0.06 mmol) in dichloromethane (1.5 ml). The mixture was stirred at room temperature for 30 min. After the completion of the reaction, the reaction solution was diluted with diethyl ether. Celite was added to the diluted solution, and the mixture was stirred at room temperature for additional 20 min. The procedure consisting of filtering the reaction mixture through Celite, adding ethyl acetate to the residue, stirring the mixture, and filtering the stirred mixture through Celite was repeated a few times. The filtrates were combined, and the solvent was removed by distillation under the reduced pressure. The residue was purified by column chromatography on silica gel (ethyl acetate:methanol=60:1) to give 2-bromoimidazo[5,1-b]thiazole-7-carbaldehyde (5 mg, 20%) as a white solid.

Example 36 (Reference Example)

A suspension of 2-bromo-7-hydroxymethylimidazo [5,1-b]thiazole (24 mg, 0.10 mmol) in dichloromethane (3.5 ml) was added to a solution of pyridinium dichromate (47 mg, 0.13 mmol) in dichloromethane (1.5 ml), and the mixture was stirred at room temperature for 5 hr. After the completion of the reaction, the reaction solution was diluted with ethyl acetate, 4A molecular sieves were added thereto, and the mixture was stirred at room temperature for 20 min. The procedure consisting of filtering the reaction mixture through Celite, adding ethyl acetate to the residue, stirring the mixture, and filtering the stirred mixture through Celite was repeated a few times. The filtrates were combined, and the solvent was removed by distillation under the reduced pressure. The residue was purified by column chromatography on silica gel (ethyl acetate:methanol=60:1) to give 2-bromoimidazo[5,1-b]thiazole-7-carbaldehyde (11 mg, 47%) as a white solid.

Example 37 (Reference Example)

Dried 4A molecular sieves (40 mg) and tetra-n-propylammonium perruthenate (16 mg, 0.05 mmol) were added to a solution of 2-bromo-7-hydroxymethylimidazo[5,1-b]thiazole (53 mg, 0.23 mmol) and N-methylmorpholine-N-oxide (92 mg, 0.79 mmol) in dichloromethane (2 ml), and the mixture was stirred at room temperature for 3 days. The reaction solution was purified by column chromatography on silica gel (ethyl acetate:methanol=60:1) to give 2-bromoimidazo[5,1-b]thiazole-7-carbaldehyde (11 mg, 21%) as a white solid.

Synthesis of
2-bromoimidazo[5,1-b]thiazole-7-carbaldehyde (II)

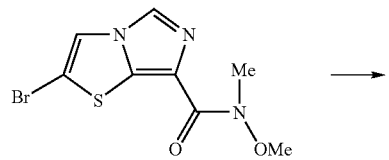

Example 38 (Reference Example)

A solution of N-methoxy-N-methyl-2-bromoimidazo[5,1-b]thiazole-7-carboxamide (54 mg, 0.19 mmol) in dichloromethane (5 ml) was cooled to −78° C. A solution of dibutylaluminium hydride in toluene (1.01 M solution; 0.4 ml, 0.42 mmol) was added dropwise to the cooled solution, and the mixture was stirred at the same temperature for 3 hr. After the completion of the reaction, a saturated aqueous potassium sodium tartrate solution was added thereto, the mixture was stirred at room temperature for one hr, and the mixture was extracted with ethyl acetate (5 ml×3). The organic layer was washed with saturated brine and was then dried over anhydrous sodium sulfate. The solvent was removed by distillation under the reduced pressure, and the residue was purified by column chromatography on silica gel (ethyl acetate:methanol=60:1) to give 2-bromoimidazo[5,1-b]thiazole-7-carbaldehyde (17 mg, 39%) as a white solid.

Synthesis of
2-bromoimidazo[5,1-b]thiazole-7-carbaldehyde (III)

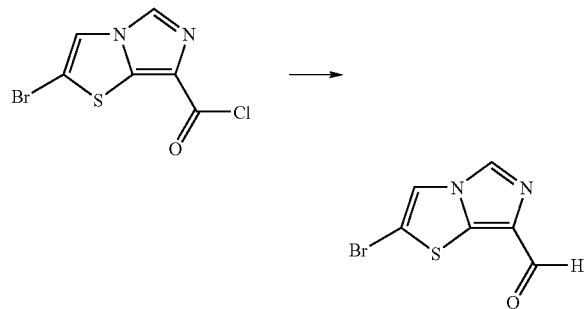

Example 39 (Reference Example)

A solution of 2-bromoimidazo[5,1-b]thiazole-7-carboxylic acid chloride (103 mg, 0.39 mmol) in diglim (10 ml) was cooled to −78° C. A solution of tri-t-butoxyaluminumlithium hydride(237 mg, 0.94 mmol) in diglim (6 ml) was added dropwise to the cooled solution, and, while gradually raising the temperature to −40° C., the mixture was stirred for 6 hr. After the completion of the reaction, a saturated aqueous ammonium chloride solution was added thereto, and the mixture was extracted with ethyl acetate (7 ml×3). The organic layer was washed with saturated brine and was then dried over anhydrous sodium sulfate. The solvent was removed by distillation under the reduced pressure, and the residue was purified by column chromatography on silica gel (ethyl acetate:methanol=60:1) to give 2-bromoimidazo[5,1-b]thiazole-7-carbaldehyde (28 mg, 31%) as a white solid.

Synthesis of N-methoxy-N-methyl-2-bromoimidazo
[5,1-b]thiazole-7-carboxamide

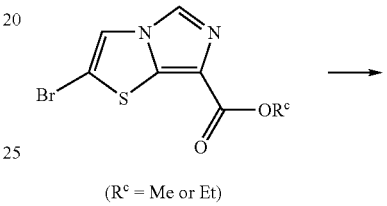

($R^c$ = Me or Et)

Example 40 (Reference Example)

Diethylaluminum chloride (0.9 M hexane solution; 1.1 ml, 1.07 mmol) was added to an ice cooled solution of N,O-dimethylhydroxylamine hydrochloride (104 mg, 1.07 mmol) in dichloromethane (4 ml), and, while gradually raising the temperature, the mixture was stirred for one hr. A solution of methyl 2-bromoimidazo[5,1-b]thiazole-7-carboxylate (56 mg, 0.21 mmol) in dichloromethane (6 ml) was added thereto, and the mixture was stirred at room temperature for 21 hr. A phosphate buffer solution (5 ml) was added to the reaction solution, and the mixture was stirred at room temperature for 10 min and was then filtered through Celite. The filtrate was washed with saturated brine and was then dried over anhydrous sodium sulfate. The solvent was removed by distillation under the reduced pressure. The residue was purified by column chromatography on silica gel (ethyl acetate:methanol=60:1→10:1) to give N-methoxy-N-methyl-2-bromoimidazo[5,1-b]thiazole-7-carboxamide (54 mg, 88%) as a white solid.

$^1$H-NMR (500 MHz, CDCl$_3$): δ 3.53 (3H, s), 3.84 (3H, s), 7.61 (1H, s), 7.97 (1H, s). $^{13}$C-NMR (125 MHz, CDCl$_3$): δ 34.4, 61.8, 108.5, 118.3, 123.9, 126.6, 137.7, 161.8. FT-IR (KBr, cm$^{-1}$): 3133, 3086, 3057, 2932, 1618, 1516, 1458, 1433, 1228, 1114, 1039, 988, 853.

Example 41 (Reference Example)

Diethylaluminum chloride (0.9 M hexane solution; 2.3 ml, 2.11 mmol) was added to an ice cooled solution of N,O-dimethylhydroxylamine hydrochloride (206 mg, 2.11 mmol) in dichloromethane (8 ml), and, while gradually raising the temperature, the mixture was stirred for one hr. A solution of ethyl 2-bromoimidazo[5,1-b]thiazole-7-carboxylate (116 mg, 0.42 mmol) in dichloromethane (4 ml) was added and stirred at room temperature for 15 hr. A phosphate buffer solution (10 ml) was added to the reaction solution, and the mixture was stirred at room temperature for 10 min and was filtered through Celite. The filtrate was washed with saturated brine and was then dried over anhydrous sodium sulfate, and the solvent was removed by distillation under the reduced pressure. The residue was purified by column chromatography on silica gel (ethyl acetate:methanol=30:1→10:1) to give N-methoxy-N-methyl-2-bromoimidazo[5,1-b]thiazole-7-carboxamide (113 mg, 92%) as a white solid.

Synthesis of 2-bromoimidazo[5,1-b]thiazole-7-carboxylic acid chloride

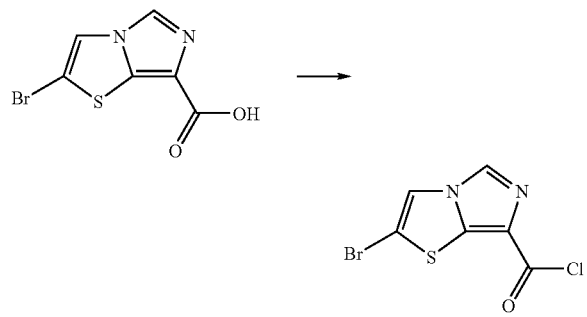

Example 42 (Reference Example)

Thionyl chloride (0.1 ml, 1.37 mmol) was added dropwise to a solution of 2-bromoimidazo[5,1-b]thiazole-7-carboxylic acid (97 mg, 0.39 mmol) in toluene (10 ml), and the mixture was heated under reflux for 1.5 hr. The excessive amount of thionyl chloride was removed at the atmospheric pressure, and the solvent was then removed by distillation under the reduced pressure to give 2-bromoimidazo[5,1-b]thiazole-7-carboxylic acid chloride (104 mg, quantitative) as a light brown solid.

$^1$H-NMR (500 MHz, CDCl$_3$): δ 7.70 (1H, s), 8.05 (1H, s).
FT-IR (neat, cm$^{-1}$): 3123, 3048, 1748, 1501, 1246, 1063, 835, 799.

The invention claimed is:
1. A compound of formula (I):

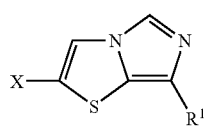

(I)

wherein
X represents a halogen atom; and
R$^1$ represents group —COR$^2$;
wherein R$^2$ represents group OM or C1-12 alkyloxy wherein M represents a hydrogen atom, an alkali metal, an alkaline earth metal, or quaternary ammonium.

2. The compound according to claim 1, wherein R$^2$ represents group OM or C1-6 alkyloxy wherein M represents a hydrogen atom, an alkali metal, an alkaline earth metal, or quaternary ammonium.

3. The compound according to claim 1, wherein X represents a bromine atom.

4. A process for producing a compound of formula (I) according to claim 1, wherein said process comprising the following steps (a) and (b):
(a) reacting a compound of formula (II) with a compound of formula (III) in the presence of a base:

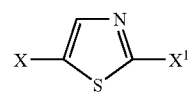

(II)

wherein X and X$^1$ each independently represent a halogen atom,

R$^3$OOCCH$_2$NC (III)

wherein R$^3$ represents C1-12 alkyl, and
(b) optionally further subjecting the compound prepared in step (a) to a hydrolysis reaction.

5. The process according to claim 4, wherein the reaction in step (a) is carried out in a temperature range of −40° C. to 50° C.

6. The process according to claim 4, wherein the hydrolysis reaction as step (b) is carried out and the compound of formula (I) is a compound of formula (V):

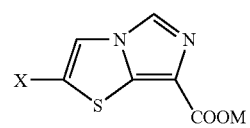

(V)

wherein X represents a halogen atom; and M represents a hydrogen atom, an alkali metal, an alkaline earth metal, or quaternary ammonium.

7. The process according to claim 4, wherein X represents a bromine atom.

8. A process for producing a compound of formula (VI),

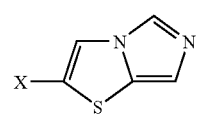

(VI)

wherein X represents a halogen atom, said process comprising heating a compound of formula (V), or a compound of formula (IV), or a compound of formula (V) prepared by hydrolyzing the compound of formula (IV):

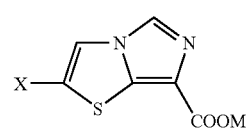

(V)

wherein X represents a halogen atom; M represents a hydrogen atom, an alkali metal, an alkaline earth metal, or quaternary ammonium, and

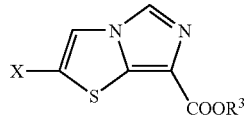
(IV)

wherein X represents a halogen atom; and $R^3$ represents C1-12 alkyl.

9. The process according to claim 8, wherein the heating temperature is in a temperature range of 100 to 300° C.

10. The process according to claim 8, wherein the reaction is carried out in a single solvent or mixed solvent having a boiling point of 100° C. or above.

11. The process according to claim 8, wherein the reaction is carried out in the presence of an additive.

12. The process according to claim 8, which further comprises reacting a compound of formula (II) with a compound of formula (III) to give the compound of formula (IV):

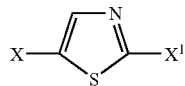
(II)

wherein X and $X^1$ each independently represents a halogen atom, and $$R^3OOCCH_2NC \quad (III)$$

wherein $R^3$ represents C1-12 alkyl.

13. The process according to claim 8, wherein X represents a bromine atom.

14. A process for producing a compound of formula (V)

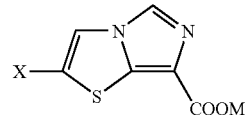
(V)

wherein X represents a halogen atom; M represents a hydrogen atom, an alkali metal, an alkaline earth metal, or quaternary ammonium, said process comprising hydrolyzing a compound of formula (IV):

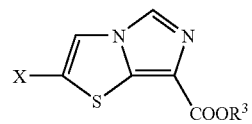
(IV)

wherein X represents a halogen atom; and $R^3$ represents C1-12 alkyl.

* * * * *